(12) United States Patent
da Conceição Moutinho et al.

(10) Patent No.: US 12,186,116 B2
(45) Date of Patent: *Jan. 7, 2025

(54) SYSTEM AND METHOD FOR DETECTING RADIATION

(71) Applicant: NU-RISE Lda, Ilhavo (PT)

(72) Inventors: Luis Miguel da Conceição Moutinho, Aveiro (PT); Joana Isabel Ferreira dos Santos Melo, Aveiro (PT)

(73) Assignee: NU-RISE Lda (PT)

( * ) Notice: Subject to any disclaimer, the term of this patent is extended or adjusted under 35 U.S.C. 154(b) by 0 days.

This patent is subject to a terminal disclaimer.

(21) Appl. No.: 18/493,466

(22) Filed: Oct. 24, 2023

(65) Prior Publication Data

US 2024/0050050 A1 Feb. 15, 2024

Related U.S. Application Data

(63) Continuation of application No. 17/682,069, filed on Feb. 28, 2022, now Pat. No. 11,801,021, which is a
(Continued)

(51) Int. Cl.
*A61B 6/42* (2024.01)
*A61B 6/00* (2024.01)
(Continued)

(52) U.S. Cl.
CPC ............ *A61B 6/42* (2013.01); *A61B 6/40* (2013.01); *A61B 6/44* (2013.01); *A61N 5/1014* (2013.01);
(Continued)

(58) Field of Classification Search
CPC .... A61B 6/42; A61B 6/40; A61B 6/44; A61B 5/1014; A61B 5/1071
See application file for complete search history.

(56) References Cited

U.S. PATENT DOCUMENTS

2010/0288934 A1* 11/2010 Keppel ................. G01T 1/204
250/362
2013/0165731 A1 6/2013 Cernica
2014/0350325 A1* 11/2014 Van Appeldoorn ....... G01T 1/02
600/8

FOREIGN PATENT DOCUMENTS

EP 3031494 A1 * 6/2016 ....... A61B 17/00234
WO WO-2013012331 A1 * 1/2013 ........... A61N 5/1001
(Continued)

OTHER PUBLICATIONS

Int'l Search Report and Written Opinion Appln No. PCT/IB2020/001025 mailed Apr. 29, 2021.

*Primary Examiner* — David P Porta
*Assistant Examiner* — Casey Bryant
(74) *Attorney, Agent, or Firm* — McAndrews, Held & Malloy, Ltd.

(57) ABSTRACT

Interstitial brachytherapy is a cancer treatment in which radioactive material is placed closely to the target tissue of the affected site using an afterloader (HDR-brachytherapy) or manually (LDR- and PDR-brachytherapy). For HDR-brachytherapy, the accuracy of this placement is calibrated using an external reference system that locates the radioactive material according to the radiation levels measured at locations around the source. At each of these locations, a scintillator produces light when irradiated by the radioactive material. This light is proportional to the level of radiation at each location. The light produced by each scintillator is converted to an electrical signal that is proportional to the light and the radiation level at each location. The radioactive material is located according to the plurality of electrical signals.

20 Claims, 8 Drawing Sheets

Related U.S. Application Data continuation of application No. 16/713,509, filed on Dec. 13, 2019, now Pat. No. 11,291,419.

(51) Int. Cl.
  *A61B 6/40* (2024.01)
  *A61N 5/06* (2006.01)
  *A61N 5/10* (2006.01)

(52) U.S. Cl.
  CPC .... *A61N 5/1071* (2013.01); *A61B 2562/0257* (2013.01); *A61B 2562/0271* (2013.01); *A61N 2005/063* (2013.01); *A61N 2005/1018* (2013.01)

(56) References Cited

FOREIGN PATENT DOCUMENTS

WO       2014/087289 A2    6/2014
WO    WO-2016093942 A2 *  6/2016   ........... A61N 5/1001

* cited by examiner

700

SYSTEM AND METHOD FOR DETECTING RADIATION

The present application is a continuation of U.S. application Ser. No. 17/682,069, filed Feb. 28, 2022, which is a continuation of U.S. application Ser. No. 16/713,509, filed Dec. 13, 2019, now U.S. Pat. No. 11,291,419. The aforementioned documents are hereby incorporated herein by reference in their entirety.

BACKGROUND

Limitations and disadvantages of conventional approaches to data storage will become apparent to one of skill in the art, through comparison of such approaches with some aspects of the present method and system set forth in the remainder of this disclosure with reference to the drawings.

BRIEF SUMMARY

Methods and systems are provided for detection and tracking of a radiation source controlled by an afterloader used for brachytherapy substantially as illustrated by and/or described in connection with at least one of the figures, as set forth more completely in the claims.

DETAILED DESCRIPTION

Brachytherapy is commonly used as an effective treatment for cervical, prostate, breast, esophageal and skin cancer, and can also be used to treat tumors in many other body sites. Interstitial brachytherapy is a cancer treatment in which radioactive material is placed closely to the target tissue of the affected site, such as in the prostate or breast.

The dose rate of brachytherapy refers to the level or intensity with which the radiation is delivered to the surrounding medium and is expressed in Grays per hour (Gy/h). In low-dose rate (LDR) brachytherapy, the rate of dose delivery typically less than 2 Gy/h. Pulsed-dose rate (PDR) brachytherapy involves short pulses of radiation, typically once an hour, to simulate the overall rate and effectiveness of LDR treatment. In high-dose rate (HDR) brachytherapy, the rate of dose delivery typically exceeds 12 Gy/h. During HDR brachytherapy, radiation sources are placed for a set duration (usually a number of seconds or minutes) before being withdrawn. The specific treatment duration will depend on many different factors, including the required isotope rate of dose delivery and the type, size and location of the cancer.

A range of imaging technologies (e.g., x-ray radiography, ultrasound, computed axial tomography (CT or CAT) scans and magnetic resonance imaging (MRI)) can be used to visualize the shape and size of the tumor and its relation to surrounding tissues and organs. The data from many of these sources can be used to create a 3D map of the tumor and the surrounding tissues. Using this information, a plan of the optimal distribution of the radiation sources can be developed. This includes consideration of how the radiation should be placed and positioned. Errors or poor treatment setup might present a safety risk to the patient. Too little irradiation or too much irradiation must be avoided during treatment, as these can result in treatment failure and severe side-effects.

Figure 1:
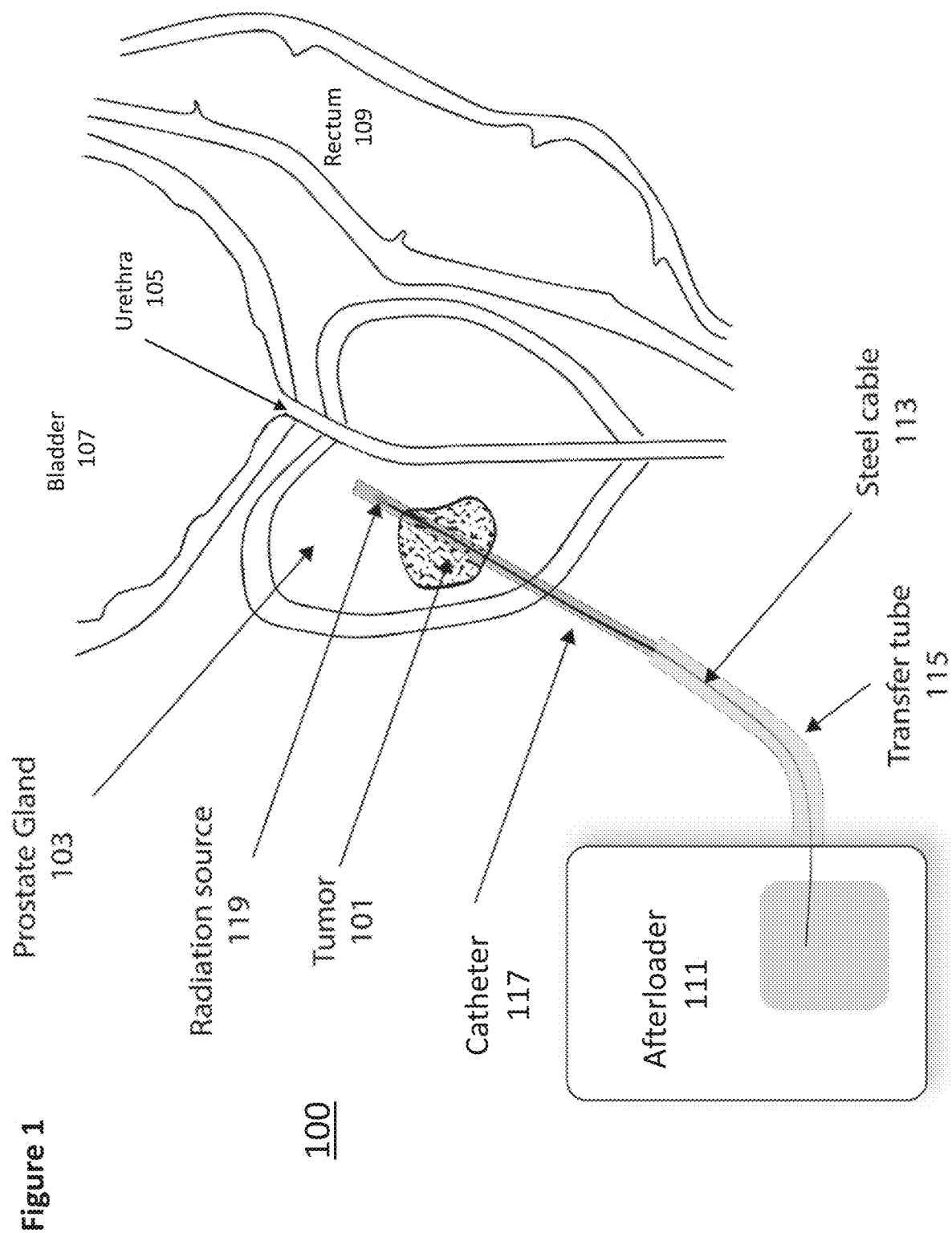
FIG. 1 illustrates an example interstitial HDR-brachytherapy treatment using an afterloader directed at a tumor in a patient's prostate in accordance with aspects of this disclosure.

FIG. 1 illustrates an example interstitial brachytherapy treatment 100 of a tumor 101 in a patient's prostate gland 103 in accordance with aspects of this disclosure. The size and location of the tumor 101 relative to the patient's urethra 105, bladder 107 and rectum 109 as shown is for illustration purposes. The tumor 101 may be any size and located anywhere in the prostate 103.

As shown in FIG. 1, an afterloader 111 is a radiotherapy machine being used to radiate the tumor 101. The afterloader 111 comprises a retractable steel cable 113. The afterloader 111 connects to a plastic or metallic catheter 117 by means of a radiation transfer tube 115. A radiation source 119 encapsulated in metal travels inside the transfer tube 115 to the catheter 117 inserted into the patient's body, close to the tumor 101. The radioactive source 119 is attached to the extremity of the steel cable 113 that is controlled by the afterloader 111. The catheter 117 receives the radiation source 119, and the afterloader 111 controls the movement, positioning and dwell time of the radiation source 119 within the tumor 101 as specified by a doctor's treatment plan.

Interstitial brachytherapy requires the precise placement of short-range radiation sources 119 (e.g., radioisotopes Cobalt-60, Iodine-125, Cesium-131, Iridium-192, etc.) directly at the site of a cancerous tumor 101. Radiation treatment is intended to kill cancerous tissue while reducing exposure to healthy tissues. The radiation source 119 may travel throughout the catheter 117 length, while stopping at pre-determined periods in specific positions, thus providing irradiation of the surrounding tissues of the tumor 101 in an isotropic way. However, if the afterloader is not properly calibrated, healthy (e.g., non-cancerous) tissues may be irradiated in error.

Figure 2A:
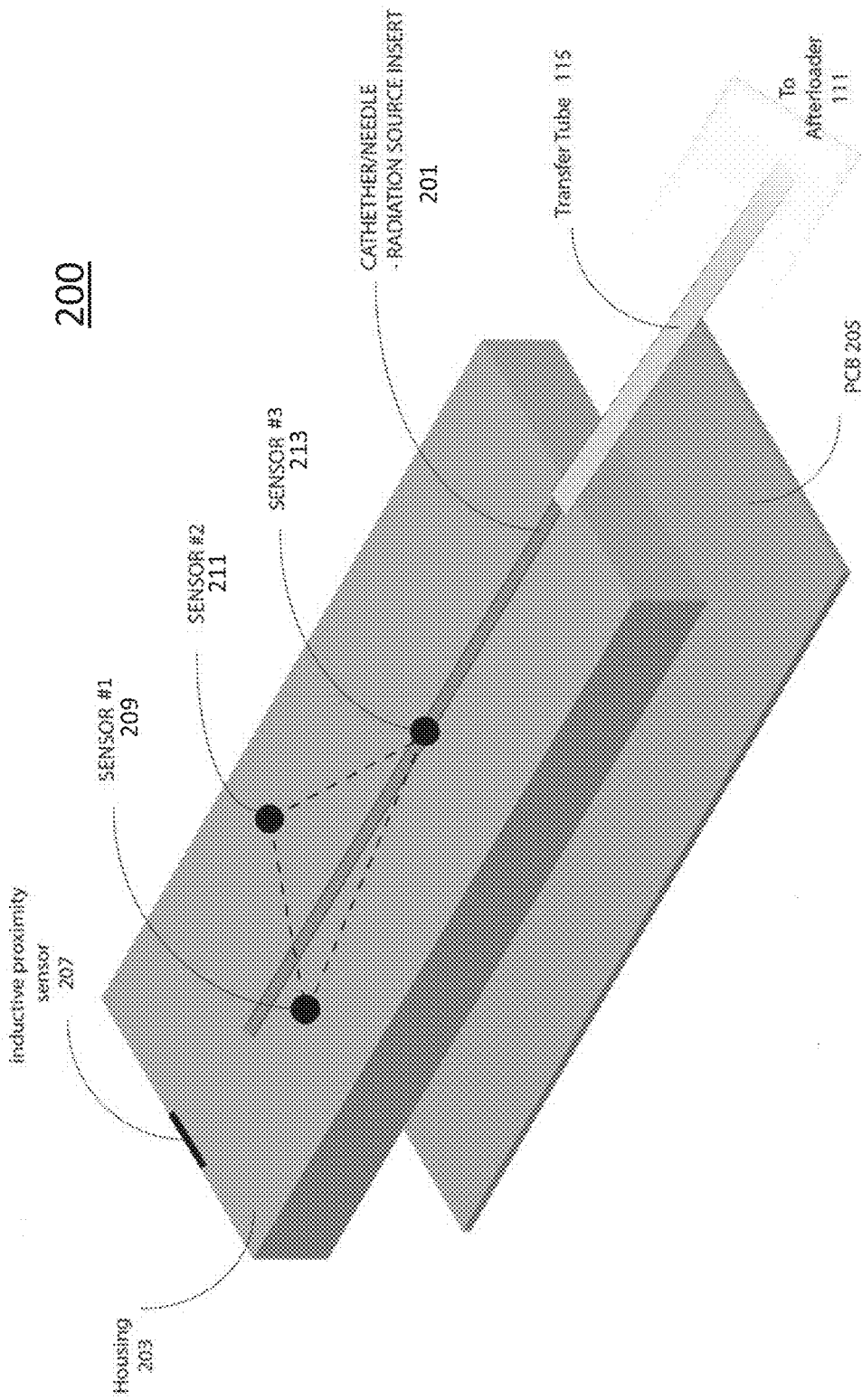
FIG. 2A illustrates a top view of an exemplary embodiment of a system for calibrating an afterloader in accordance with aspects of this disclosure.
Figure 2B:
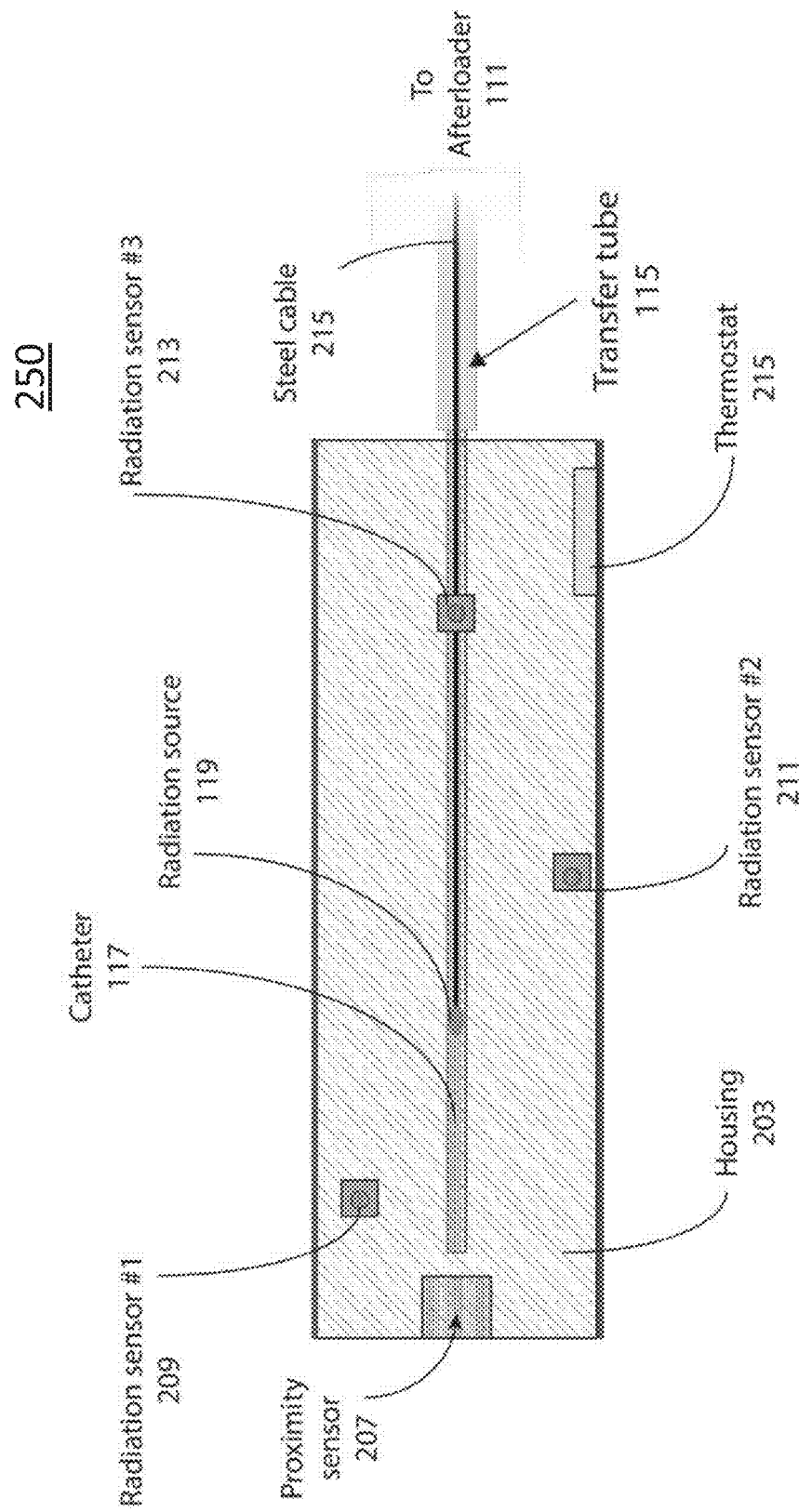
FIG. 2B illustrates a top view of another exemplary embodiment of a system for calibrating an afterloader in accordance with aspects of this disclosure.

Aspects of the present disclosure provide a tool for calibration of an afterloader radiotherapy machine to provide accurate radiation source position calibration and activity and dose calibration. FIG. 2A illustrates a top view of an exemplary embodiment of a system 200 for calibrating an afterloader in accordance with aspects of this disclosure. FIG. 2B illustrates a top view of another exemplary embodiment of a system 250 for calibrating an afterloader in accordance with aspects of this disclosure.

The calibration systems 200 and 250 include a water-equivalent housing 203 on a printed circuit board (PCB) 205. A proximity sensor 207 is located at one end of the housing 203, and three radiation sensors 209, 211 and 213 are placed within the housing 203. To calibrate the afterloader and identify the optimal spatial and temporal distribution of radiation provided by an afterloader 111, an afterloader catheter 117 is inserted into the calibration system housing 203 at insertion point 201 and a radiation source 119 is directed through the calibration system 200 while radiation is measured by radiation sensors 209, 211 and 213. The proximity sensor 207 may also measure the distance to the radiation source 119 that is encapsulated in metal. The embodiment 250 in FIG. 2B illustrates that the three radiation sensors 209, 211 and 213 may be placed at various locations. Additionally, FIG. 2B shows that a calibration system may use a thermostat 215 to measure the temperature of the system 250 during calibration.

Figure 3:
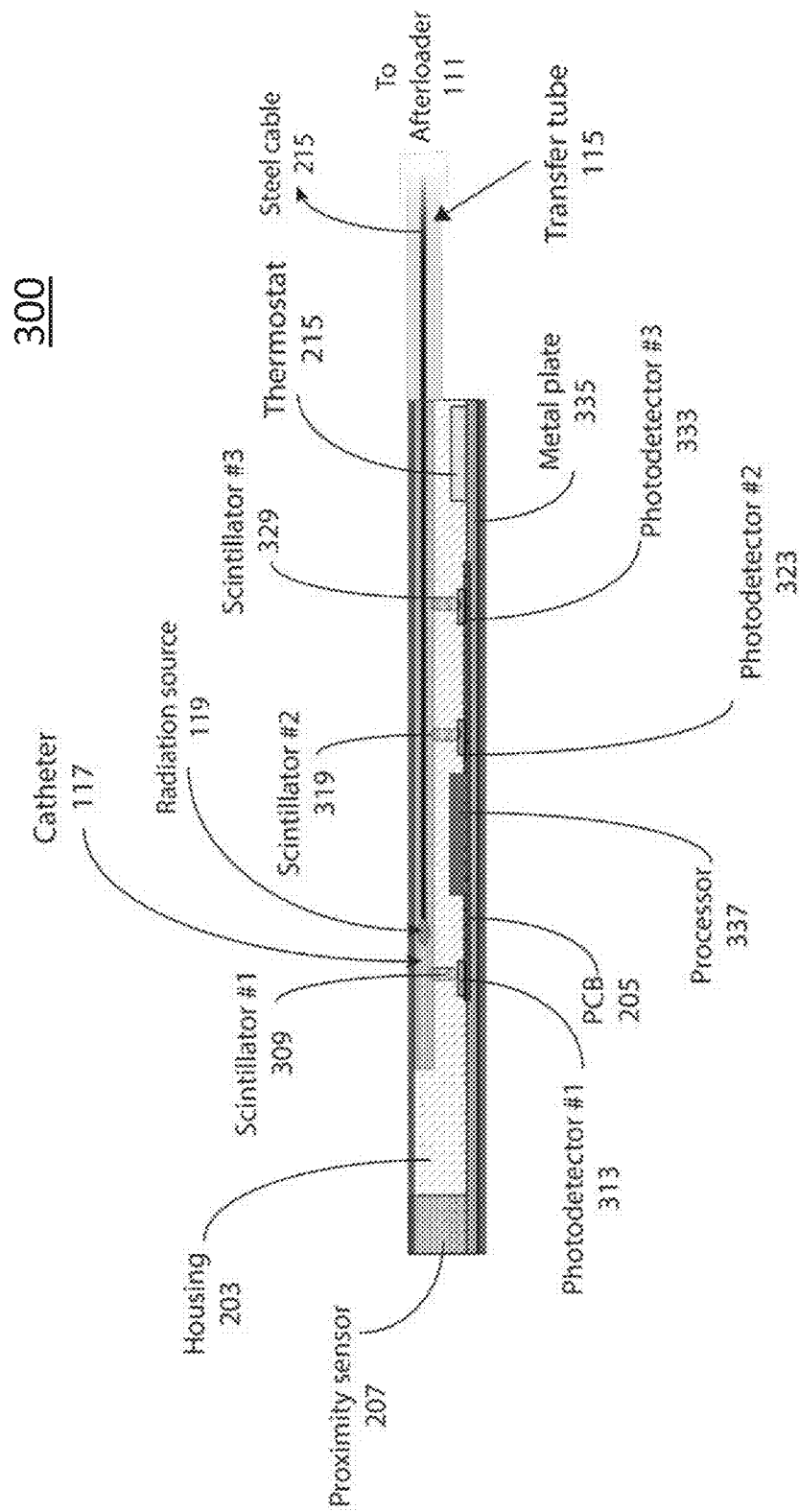
FIG. 3 illustrates a partially opened side view of an exemplary embodiment of a system for calibrating an afterloader in accordance with aspects of this disclosure.

FIG. 3 illustrates a partially opened side view of an exemplary embodiment of a system for calibrating an afterloader in accordance with aspects of this disclosure. FIG. 3 shows that a calibration system may use a metal plate 335. Additionally, FIG. 3 shows that each of the three radiation sensors (209, 211, 213 in FIGS. 2A and 2B) may comprise a scintillator 309, 319, 329 and a photodetector 313, 323, 333 respectively.

Aspects of the present disclosure provide systems (e.g., systems 200, 250 and 300 illustrated in FIGS. 2A, 2B and 3) for detecting radiation produced by a radiation source that is controlled by an afterloader. The intensity, position and velocity of the detected radiation can be used as feedback to calibrate the afterloader.

As shown in FIG. 3, each of the plurality of scintillators 309, 319, 329 are positioned near each of the plurality of light detection units 313, 323, 333. Each scintillator 309, 319, 329 is configured to produce light in a presence of radiation from a radioactive source of radiation 119. The level of the light produced by each scintillator 309, 319, 329 is proportional to the level of the radiation incident to each scintillator 309, 319, 329. The characteristics (or nature) of the scintillators signal produced is dependent on the type of radiation. For example, gamma, x-rays and protons will produce different signals. Light signals produced according one type of radioactive material may have a spectrum that differs from the spectrum of light signals produced according another type of radioactive material. Each light detection unit 313, 323, 333 is configured to produce an electrical signal in a presence of the light from one scintillator of the plurality of scintillators 309, 319, 329. The level of the electrical signal produced by each light detection unit 313, 323, 333 is proportional to the light incident to each light detection unit 313, 323, 333. Thus the level of the electrical signal produced by each light detection unit 313, 323, 333 is proportional to the level of the radiation incident to each scintillator 309, 319, 329. Each light detection unit of the plurality of light detection units 313, 323, 333 may be located near coupled to one scintillator of the plurality of scintillators 309, 319, 329 via an optical fiber.

A processor 337 is configured to calculate a location of the radiation source according to the electrical signals from the plurality of light detection units 313, 323, 333. The processor 337 may be configured to calculate the location of the radiation source by trilateration (or triangulation) according to the electrical signals from the plurality of light detection units 313, 323, 333. The processor may also be configured to calculate a velocity of the radiation source 119 according to the electrical signals from the plurality of light detection units.

The plurality of scintillators 309, 319, 329 may be enclosed in a water-equivalent housing 203. The radiation source 119 may be selectively inserted into the water-equivalent housing 203 via a probe (e.g., plastic or metal catheter 117) of the afterloader. The water-equivalent housing 203 may comprise an inductive proximity detector 207 configured to detect a presence of the probe in the water-equivalent housing. Placement of the catheter 117 may be detected by the proximity sensor 207. A movement of the radiation source 119 may be detected by the proximity sensor 207. To maintain a constant temperature of the system 300 during radiation measurement, the temperature of the metal plate 335 is controlled by the thermostat 215.

Figure 4A:
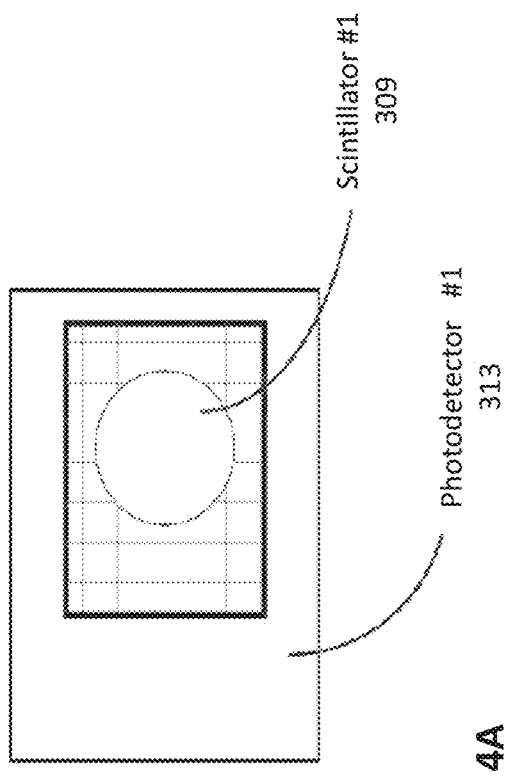
FIG. 4A illustrates an exemplary radiation sensor in a system for calibrating an afterloader in accordance with aspects of this disclosure.

FIG. 4A illustrates an exemplary radiation sensor in a system for calibrating an afterloader in accordance with aspects of this disclosure. According to one embodiment, the radiation sensor 209 comprises a scintillator 309 and a photodetector 313. The scintillator 309 collects radiation and converts this radiation into a luminous signal with an intensity that is proportional to the level of incident radiation. The scintillator 309 may be an organic scintillator (e.g., BC-400, BC-404, BC-412, and BCF-12 as manufactured by Saint-Gobain) or an inorganic scintillators. BCF-12, for example, is a scintillating optical fibre. The photodetector 313 is located near the scintillator 309 and converts the luminous signal into an electrical signal (e.g., voltage or current) with a magnitude that is proportional to the level of incident illumination. The photodetector 313 typically comprises a fast signal response to allow for identification of a scintillator 309 luminous signal proportional to the radiation source strength and relative position. For example, a radiation source (e.g., iridium 192) will decay over time and the use of three photodetectors 313, 323 and 333 and three scintillators 309, 319 and 329 may be used to determine the radiation source strength and relative position.

Figure 4B:
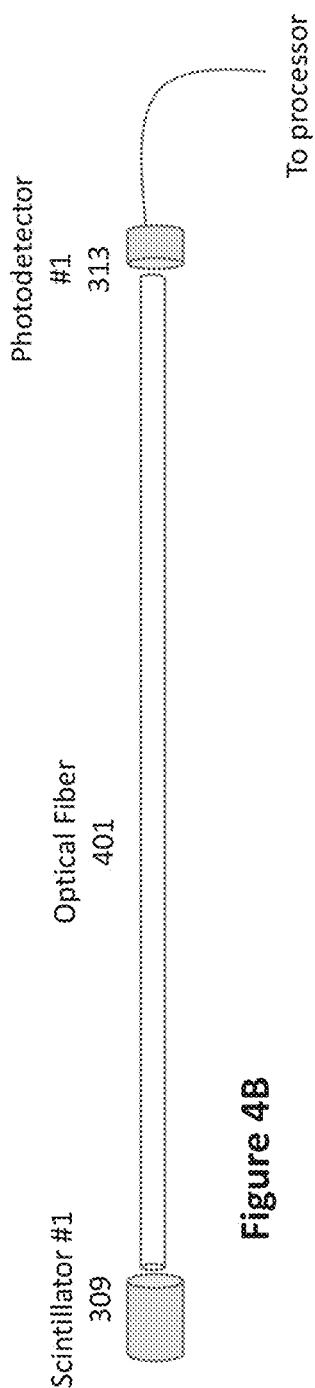
FIG. 4B illustrates another exemplary radiation sensor in a system for calibrating an afterloader in accordance with aspects of this disclosure.

FIG. 4B illustrates another exemplary radiation sensor in a system for calibrating an afterloader in accordance with aspects of this disclosure. The photodetector 313 (e.g., photodiode) may be coupled to the scintillator 309 via an optical fiber 401. The photodetector 313 may also comprise a built-in lens and/or optical filter window to select one or more wavelengths emitted from a particular scintillator 309.

Figure 5:
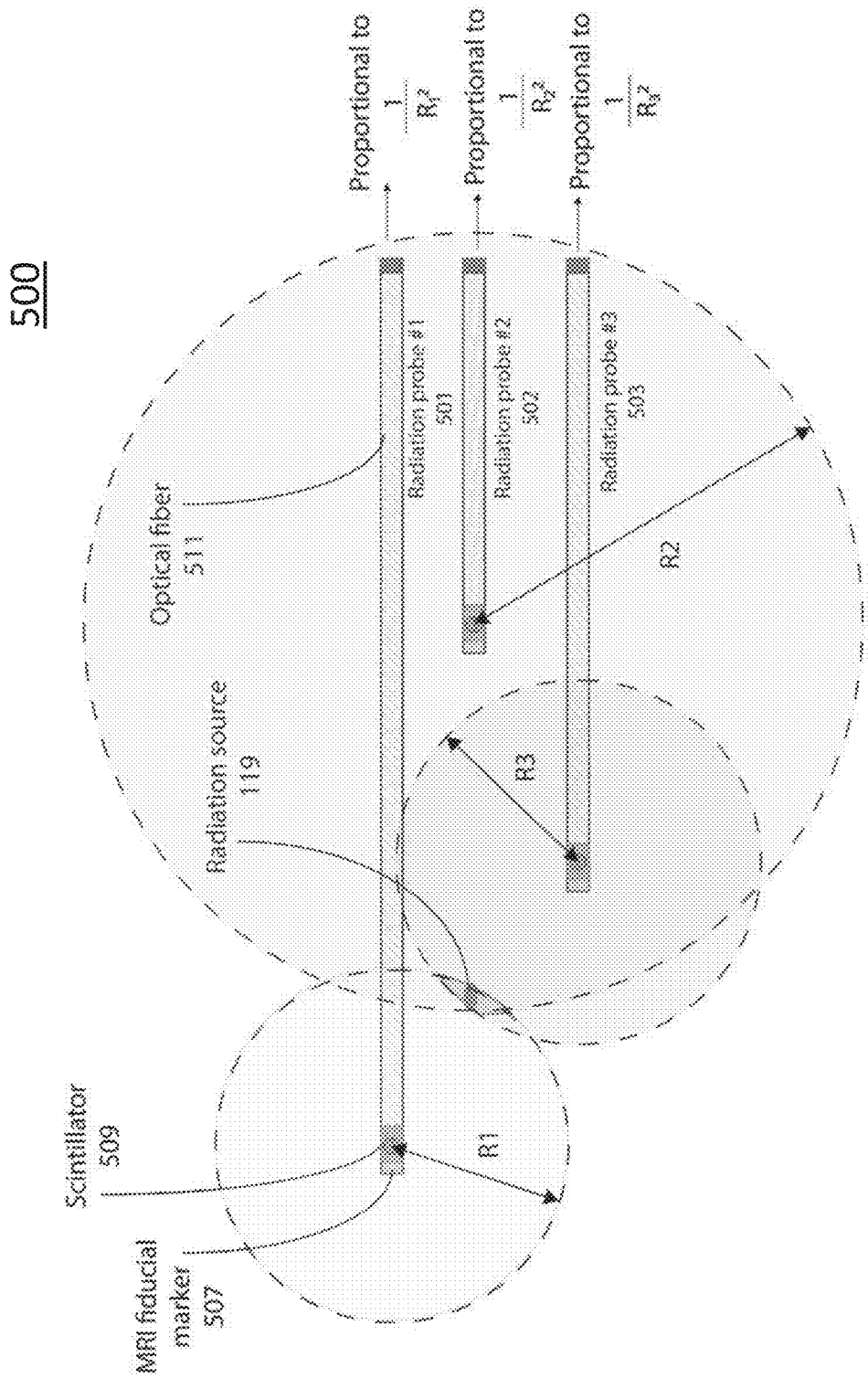
FIG. 5 illustrates a first exemplary arrangement of radiation sensors in a system for calibrating an afterloader in accordance with aspects of this disclosure.

FIG. 5 illustrates a first exemplary arrangement 500 of radiation sensors in a system for calibrating an afterloader in accordance with aspects of this disclosure. According to an example embodiment, the radiation source detector of a calibration system is capable to determine the position of a radiation source 119 by trilateration. The system can be used to calibrate afterloader radiation source positioning inside a plastic or metallic tube such as a catheter.

The exemplary arrangement 500 in FIG. 5 comprises radiation probe #1 501, radiation probe #2 503, and radiation probe #3 505. These probes may be used in calibration systems 200, 250 and 300 as described with respect to FIGS. 2A, 2B and 3. Radiation probe #1 501 is illustrated with further detail. Radiation probe #1 501 comprises a scintillator 509 and a photodetector 513 that operate is a similar way as scintillator 309 and a photodetector 313 in FIG. 4. Additionally, radiation probe #1 501 may also comprise a fiducial marker 507 and/or an optical fiber 511. The fiducial marker 507 may comprise a gold piece that allows the radiation probe #1 501 to be located with an imaging scanner, such as an MRI or CT scanner. The optical fiber 511 allows the photodetector 513 to be located at a distance from the scintillator 509.

When the radiation source 119 is in proximity, radiation probe #1 501, radiation probe #2 503, and radiation probe #3 505 produces an electrical signal that is inversely proportional to a function of the distance R1, R2, R3 between the radiation source 119 and the scintillator of each respective radiation probe 501, 503, 505. For example, an electrical signal thus produced may be inversely proportional to the square of the distance between radiation source 119 and the point 509 where radiation is converted to light. Each calculated distances R1, R2, R3 produces a sphere 541, 543, 545 of possible locations of radiation source 119. The intersection of the spheres 541, 543, 545 identify the radiation source 119 location.

Figure 6:
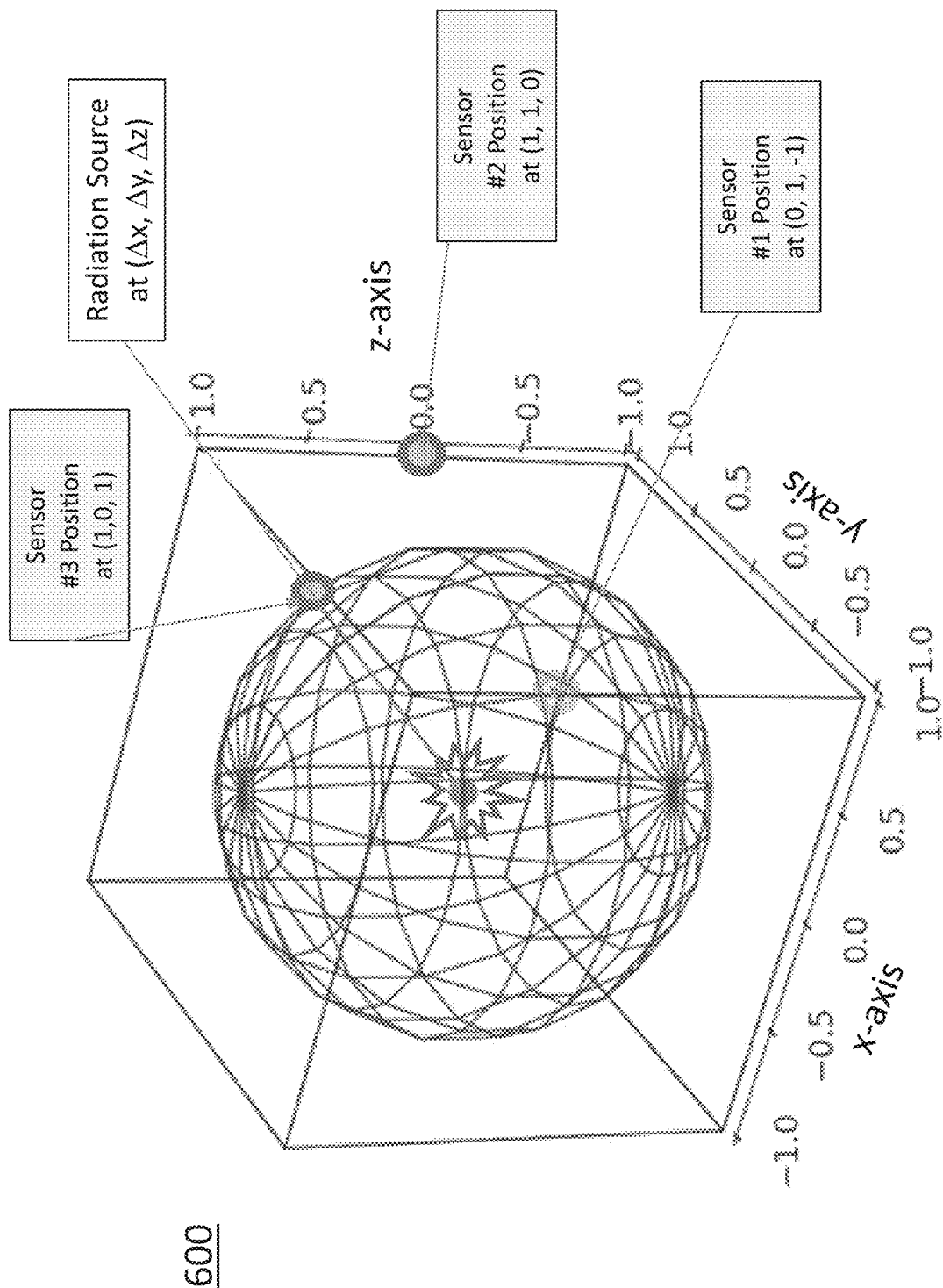
FIG. 6 illustrates a second exemplary arrangement of radiation sensors in a system for calibrating an afterloader in accordance with aspects of this disclosure.

FIG. 6 illustrates a second exemplary arrangement 600 of radiation sensors in a system for calibrating an afterloader in accordance with aspects of this disclosure. For example, the expected location of the radiation source 119 controlled by afterloader 111 of FIG. 1 may be designated in Cartesian coordinates as (0, 0, 0). If the afterloader 111 is not calibrated, the actual location of the radiation source 119 may be different than the expected location. The difference between the actual location of the radiation source 119 and the expected location may be designated in Cartesian coordinates as ($\Delta$x, $\Delta$y, $\Delta$z) as shown in FIG. 6. An embodiment with the sensors located at (0, 1, −1), (1, 1, 0) and (1, 0, 1) will be described in conjunction with FIG. 7.

Figure 7:
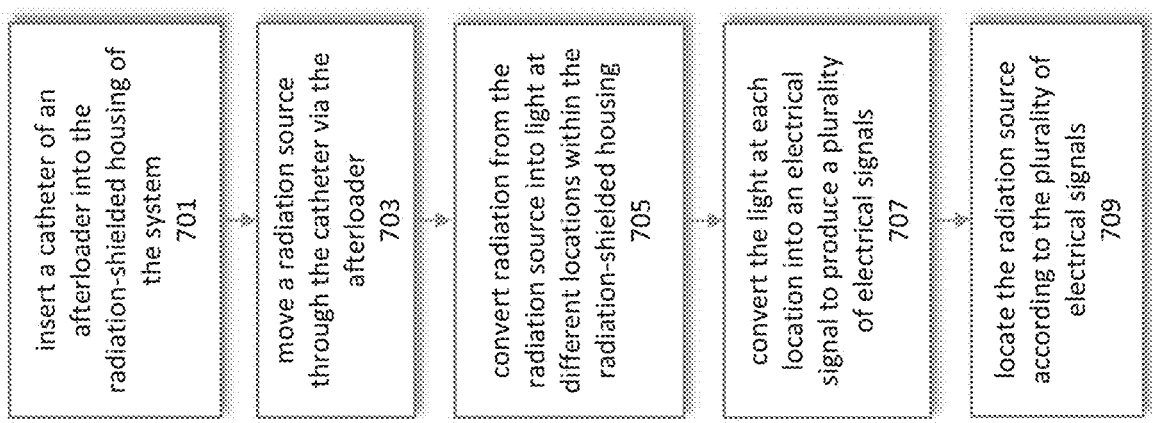
FIG. 7 illustrates an exemplary method for calibrating an afterloader in accordance with aspects of this disclosure.

FIG. 7 illustrates an exemplary method 900 for detecting radioactive material and calibrating an afterloader in accordance with aspects of this disclosure. The method 700 comprises inserting a catheter of the afterloader into a water-equivalent housing at 701. Once the catheter is received by the housing, a radiation source is moved through the catheter via the afterloader at 703. The temperature of the PCB may be maintained by a thermostat connected to a temperature-controlled metal plate that extends through the housing.

A plurality of scintillators are located at different locations within the water-equivalent housing. Each scintillator is used to convert radiation from the radiation source into a light signal at 705. A level of the light produced by each scintillator is proportional to a level of the radiation incident at each of the plurality of locations. The plurality of scintillators are enclosed in the water-equivalent housing.

The light produced by each scintillator is converted to an electrical signal using each of a plurality of light detection units (e.g., photodetectors) at 707. A level of the electrical signal produced by each light detection unit is proportional to the light incident to each light detection unit. Each light detection unit of the plurality of light detection units is coupled to one scintillator of the plurality of scintillators. The light detection units may be located within the housing. Alternatively, each light detection unit may be coupled to one scintillator via an optical fiber, and the light detection units can be placed outside of the housing.

At 709, a processor is operable to calculate a location of the radiation source according to the electrical signals from the plurality of light detection units. The location of the radiation source may be determined according to the electrical signals from the plurality of light detection units. The velocity of the radiation source may also be calculated according to the electrical signals from the plurality of light detection units and the known distances between each scintillator.

While the present method and/or system has been described with reference to certain implementations, it will be understood by those skilled in the art that various changes may be made and equivalents may be substituted without departing from the scope of the present method and/or system. In addition, many modifications may be made to adapt a particular situation or material to the teachings of the present disclosure without departing from its scope. Therefore, it is intended that the present method and/or system not be limited to the particular implementations disclosed, but that the present method and/or system will include all implementations falling within the scope of the appended claims.

As utilized herein the terms "circuits" and "circuitry" refer to physical electronic components (i.e. hardware) and any software and/or firmware ("code") which may configure the hardware, be executed by the hardware, and or otherwise be associated with the hardware. As used herein, for example, a particular processor and memory may comprise first "circuitry" when executing a first one or more lines of code and may comprise second "circuitry" when executing a second one or more lines of code. As utilized herein, "and/or" means any one or more of the items in the list joined by "and/or". As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z". As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled or not enabled (e.g., by a user-configurable setting, factory trim, etc.).

What is claimed is:

1. A system for detecting radiation, the system comprising:
    a radiation-shielded housing configured to receive a catheter comprising a radiation source;
    a scintillator, in the radiation-shielded housing, configured to produce light according to radiation from the radiation source;
    a light detection unit configured to produce an electrical signal according to the light from the scintillator; and
    a processor configured to determine a location of the radiation source according to the electrical signal from the light detection unit.

2. The system of claim 1, wherein the scintillators is enclosed in a water-equivalent housing and the radiation source is selectively inserted into the water-equivalent housing via the catheter.

3. The system of claim 2, wherein the water-equivalent housing comprises an inductive proximity detector configured to indicate a distance to the radiation source.

4. The system of claim 2, wherein the water-equivalent housing comprises a thermostat configured to maintain a constant temperature.

5. The system of claim 4, wherein the water-equivalent housing comprises a metal plate configured to regulate the constant temperature according to the thermostat.

6. The system of claim 1, wherein the processor is configured to determine the location of the radiation source according to a change in the electrical signal over time.

7. The system of claim 1, wherein the light detection unit is a photodetector.

8. The system of claim 1, wherein the light detection unit is coupled to the scintillator.

9. The system of claim 8, wherein the light detection unit is coupled to the scintillator via an optical fiber.

10. The system of claim 1, wherein the processor is configured to determine a velocity of the radiation source according to the electrical signal from the light detection unit.

11. A method for detecting radiation comprising:
moving a radiation source through a catheter in a radiation-shielded housing;
converting radiation from the radiation source into light via a scintillator;
converting the light into an electrical signal via a light detection unit; and
determining, via a processor, a location of the radiation source according to the electrical signal from the light detection unit.

12. The method of claim 11, wherein the radiation-shielded housing comprise a water-equivalent housing.

13. The method of claim 11, wherein the method comprises detecting a presence of the radioactive source in the radiation-shielded housing using an inductive proximity detector.

14. The method of claim 11, wherein the method comprises maintaining a constant temperature in the radiation-shielded housing using a thermostat.

15. The method of claim 14, wherein the method comprises regulating the constant temperature via a metal plate.

16. The method of claim 11, wherein the method comprises determining the location of the radiation source according to a change in the electrical signal over time.

17. The method of claim 11, wherein the light detection unit is a photodetector.

18. The method of claim 11, wherein the light detection unit is coupled to the scintillator.

19. The method of claim 18, wherein the light detection unit is coupled to the scintillator via an optical fiber.

20. The method of claim 11, wherein the method comprises determining a velocity of the radiation source according to the electrical signal from the light detection unit.

* * * * *